United States Patent
Wang et al.

(10) Patent No.: US 12,292,367 B1
(45) Date of Patent: May 6, 2025

(54) IMAGING DEVICE AND METHOD FOR TURBID OIL ABRASIVE PARTICLES BASED ON POLARIZED IMAGE ENHANCEMENT

(71) Applicant: SHANDONG UNIVERSITY, Jinan (CN)

(72) Inventors: Liming Wang, Jinan (CN); Yu Du, Jinan (CN); Yanyan Nie, Jinan (CN); Fangyi Li, Jinan (CN); Zihan Ye, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 18/974,563

(22) Filed: Dec. 9, 2024

(30) Foreign Application Priority Data

Apr. 24, 2024 (CN) .......................... 202410494094.6

(51) Int. Cl.
G01N 15/0227 (2024.01)
G01N 15/0205 (2024.01)
G01N 15/00 (2006.01)
G01N 15/02 (2006.01)

(52) U.S. Cl.
CPC ..... G01N 15/0227 (2013.01); G01N 15/0211 (2013.01); G01N 2015/0053 (2013.01); G01N 15/0272 (2013.01)

(58) Field of Classification Search
CPC ........... G01N 15/0227; G01N 15/0211; G01N 15/0272; G01N 2015/0053
See application file for complete search history.

(56) References Cited

FOREIGN PATENT DOCUMENTS

CN 112697800 A 4/2021
CN 117054296 A 11/2023

OTHER PUBLICATIONS

Title of the Item: Acta Physica Sinica Publication Date: Dec. 31, 2015 Name of the Author: Guan Jin-Ge, Zhu Jing-Ping, Tian Heng, Hou Xun Article Title: Real-time polarization difference underwater imaging based on Stokes vector pp. P1-P7.

Primary Examiner — Rebecca C Bryant
(74) Attorney, Agent, or Firm — George D. Morgan

(57) ABSTRACT

Provided in the present invention are an imaging device and method for turbid oil abrasive particles based on polarized image enhancement, which belong to the technical field of image processing. The imaging device of the present invention includes a CMOS fixing device, a Stokes polarized CMOS sensor, an optical lens sleeve and an optical magnifying glass, where the Stokes polarized CMOS sensor includes a CMOS sensor and a Stokes analyzer. By using a polarization characteristic difference between scattered light of lubricating oil media and reflected light of abrasive particles, Stokes vector information is measured in real time under turbid lubricating oil scenes, the scattered light of the media is filtered out, image quality of the abrasive particles is improved, coverage duration for monitoring abrasive particle imaging is effectively prolonged.

6 Claims, 8 Drawing Sheets

IMAGING DEVICE AND METHOD FOR TURBID OIL ABRASIVE PARTICLES BASED ON POLARIZED IMAGE ENHANCEMENT

CROSS-REFERENCE TO RELATED APPLICATIONS

The application claims priority to Chinese patent application No. 202410494094.6, filed on Apr. 24, 2024, the entire contents of which are incorporated herein by reference.

TECHNICAL FIELD

The present invention relates to the technical field of image processing, and in particular to an imaging device for turbid oil abrasive particles based on polarized image enhancement, an imaging system for turbid oil abrasive particles based on polarized image enhancement, and an imaging method for turbid oil abrasive particles based on polarized image enhancement.

BACKGROUND

This statement merely provides background art related to the present invention and does not necessarily constitute the prior art.

As working duration increases, lubricating oil in rotating machinery equipment often darkens in color due to high-temperature oxidation, pollution impurities and other reasons, gradually changing from light yellow to dark brown, transparency gradually decreases, and the lubricating oil becomes turbid. Capturing appearance characteristics of abrasive particles in lubrication lines of equipment by an optical imaging method is a mainstream method for on-line abrasive particle monitoring. However, the lubricating oil will gradually become turbid and black due to oxidation and impurities over time, which poses difficulties for imaging and subsequent image processing of abrasive particles. Moreover, optical imaging sensors are extremely sensitive to color and turbidity of the lubricating oil. When the lubricating oil that has been in use for a relatively long time is monitored, the shot abrasive particles are blurred or even the abrasive particles cannot be captured. Information of the abrasive particles cannot be effectively restored by existing fuzzy image processing methods, resulting in a significant decrease in detection efficiency and accuracy. Main reasons are that:

An imaging part of the current optical imaging sensor mainly consists of active lighting equipment and a camera. When entering transparent lubricating oil, lighting light is reflected by the abrasive particles and returns to a CMOS sensor of the camera, and the returned light is mainly direct reflected light of the abrasive particles, such that the abrasive particles are displayed clearly. However, turbid lubricating oil contains a large number of tiny particles, a scattering effect will be produced after the light is incident, resulting in a large amount of weak scattered light and diffuse scattered light, the weak scattered light and the diffuse scattered light are mixed and overlaid with the reflected light of the abrasive particles, and then return to the CMOS sensor of the camera, causing the image of the abrasive particles to be blurred and the imaging quality to decrease. Because light information of the abrasive particles has been lost in a scattering process, true appearance characteristics of the abrasive particles cannot be reflected by existing image enhancement or restoration processing methods.

SUMMARY

In order to solve the deficiencies of the prior art, the present invention provides an imaging device and method for turbid oil abrasive particles based on polarized image enhancement. By using a polarization characteristic difference between scattered light of lubricating oil media and reflected light of abrasive particles, Stokes vector information is measured in real time under turbid lubricating oil scenes, the scattered light of the media is filtered out, image quality of abrasive particles is improved, coverage duration for monitoring abrasive particle imaging is effectively increased, and technical support is provided for judgment of abrasive particles at an abrasive stage and abrasive particles at a health status.

To achieve the above objective, the present invention adopts the following technical solutions:

in a first aspect, the present invention provides an imaging device for turbid oil abrasive particles based on polarized image enhancement.

The imaging device for turbid oil abrasive particles based on polarized image enhancement includes a CMOS fixing device, a Stokes polarized CMOS sensor, an optical lens sleeve and an optical magnifying glass, where the Stokes polarized CMOS sensor includes a CMOS sensor and a Stokes analyzer;

the Stokes analyzer includes a plurality of linear polarization units in different polarization directions, and all the linear polarization units are in one-to-one correspondence in pixels with the CMOS sensor;

the optical lens sleeve is connected to the CMOS fixing device, the optical magnifying glass is provided at a tail end of the optical lens sleeve, and the CMOS fixing device is fixedly connected to a housing; and a circular polarized light source is fixed inside the housing, optical glass connected to the inner wall of the housing is provided below the circular polarized light source, a gap between the bottom of the optical glass and the inner wall of the housing serves as the lubricating oil flow channel, and the inlet and the outlet of the lubricating oil flow channel are both formed in the housing.

As a further limitation to the first aspect of the present invention, a white diffused reflection coating is sprayed onto the flow channel bottom of the lubricating oil flow channel.

As a further limitation to the first aspect of the present invention, different polarization directions are a 0° polarization direction, a 45° polarization direction, a 90° polarization direction, and a 135° polarization direction.

As a further limitation to the first aspect of the present invention, the circular polarized light source includes a circuit board, a circular white light source and a linear polarizer from top to bottom, the circuit board is connected to the circular white light source, and light from the circular white light source passes through the linear polarizer and changes from unpolarized natural white light to linearly polarized light with a specific polarization direction.

As a further limitation to the first aspect of the present invention, the housing is an aluminum alloy housing.

In a second aspect, the present invention provides an imaging system for turbid oil abrasive particles based on polarized image enhancement.

The imaging system for turbid oil abrasive particles based on polarized image enhancement includes an equipment lubricating pipeline, a lubricating oil branch, an oil pump, a control terminal, and the imaging device for turbid oil abrasive particles based on polarized image enhancement according to the first aspect of the present invention, where the equipment lubricating pipeline is in communication with the lubricating oil branch, the oil pump is connected to the lubricating oil branch, and the lubricating oil branch is in communication with an inlet and an outlet of a lubricating oil flow channel, and then is in communication with the equipment lubricating pipeline; and the control terminal is connected to the Stokes polarized CMOS sensor and the oil pump, respectively.

As a further limitation to the second aspect of the present invention, the control terminal is in wired communication connection or wireless communication connection with an upper computer.

In a third aspect, the present invention provides an imaging method for turbid oil abrasive particles based on polarized image enhancement.

The imaging method for turbid oil abrasive particles based on polarized image enhancement, using the imaging system for turbid oil abrasive particles based on polarized image enhancement according to the second aspect of the present invention, includes the following process:

the oil pump operates at a set speed and starts the circular polarized light source with first set light intensity, and the Stokes polarized CMOS sensor acquires an initial image and calculates an average gray value of the initial image:

if the average gray value is less than a set threshold, the light intensity of the circular polarized light source is adjusted to second set light intensity, after set time of shooting, image frames are extracted, polarized images are extracted according to the image frames, the Stokes vectors and the angle of polarization of the background light are calculated, and the polarized abrasive particle image is obtained according to the Stokes vectors and the angle of polarization of the background light; and if the average gray value is greater than or equal to the set threshold, after set time of shooting, the image frames are extracted, and the unpolarized abrasive particle image is obtained according to the image frames.

As a further limitation to the third aspect of the present invention, the polarized images are images in the 0° polarization direction, images in the 45° polarization direction, images in the 90° polarization direction, and images in the 135° polarization direction, the first set light intensity is $I_0$, and the second set light intensity is $$\frac{3}{2} I_0;$$

An image $I_{PD}$ of polarized abrasive particles is: $I_{PD} = S_1 (T) \sin 2\theta_B - S_2 (T) \cos 2\theta_B$, where $S_1$ (T) is a light intensity difference between a 0° polarization component and a 90° polarization component of the target signal light, $S_2$ (T) is a light intensity difference between a 45° polarization component and a 135° polarization component of the target signal light, and $\theta_B$ is a polarization direction of the background light.

As a further limitation to the third aspect of the present invention, the polarization direction $\theta_B$ of the background light is $$\theta_B = \frac{1}{2} \arctan \frac{S_1(B)}{S_2(B)},$$

where $S_1$ (B) is a light intensity difference between a 0° polarization component and a 90° polarization component of background scattered light, and $S_2$ (B) is a light intensity difference between a 45° polarization component and a 135° polarization component of the background scattered light.

Compared with the prior art, the present invention has the following beneficial effects:

1. the present invention creatively proposes an imaging device and method for turbid oil abrasive particles based on polarized image enhancement. By using a polarization characteristic difference between scattered light of lubricating oil media and reflected light of abrasive particles, Stokes vector information is measured in real time under turbid lubricating oil scenes, the scattered light of the media is filtered out, image quality of abrasive particles is improved, the effectiveness of an abrasive particle imaging method in high-turbidity lubricating oil is improved, coverage duration for monitoring abrasive particle imaging is effectively prolonged, and a technical support is provided for judgment of abrasive particles at an abrasive stage and abrasive particles at a health status.

2. The present invention creatively proposes an imaging device and method for turbid oil abrasive particles based on polarized image enhancement. Stokes vector information of low-transparency oil background light is acquired in real time through the Stokes polarized CMOS sensor, such that position errors caused by manual rotation of polarizers are avoided, and polarization imaging accuracy and equipment automation are improved.

The additional advantages of the present invention will be partially presented in the following description, some of which will become apparent from the following description, or learned through practice of the present invention.

BRIEF DESCRIPTION OF THE DRAWINGS

The accompanying drawings of the specification which constitute a part of the present invention provide further understanding of the present invention. The schematic embodiments of the present invention and description thereof are intended to explain the present invention and are not intended to constitute an improper limitation of the present invention.

Figure 1:
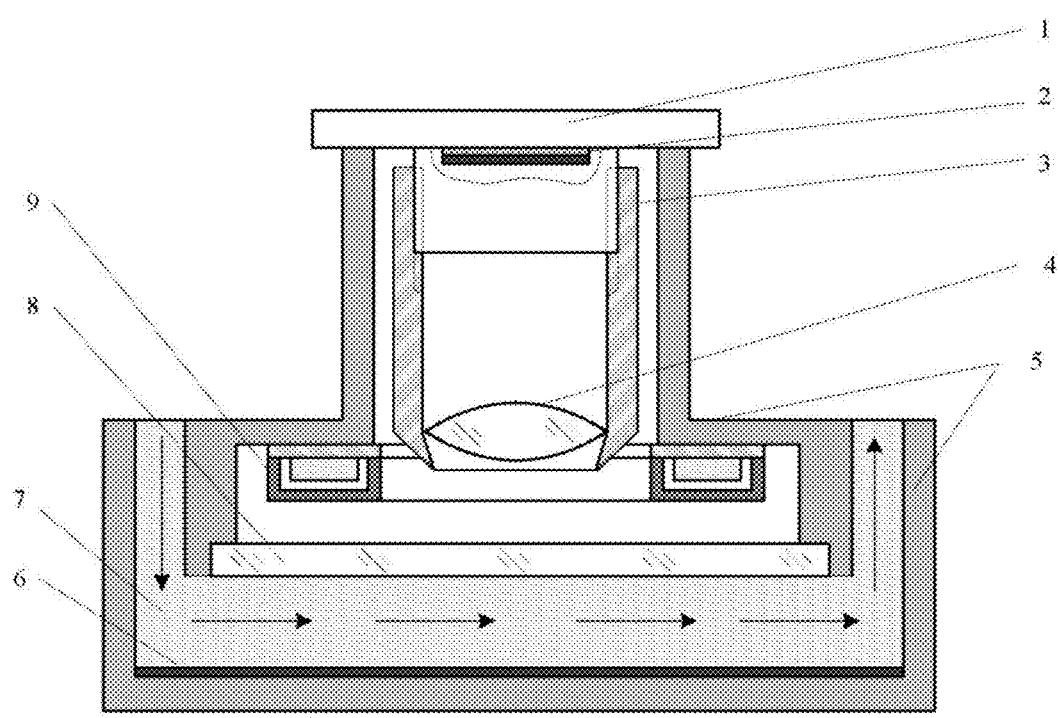
FIG. 1 shows a schematic diagram of an imaging device for turbid oil abrasive particles based on polarized image enhancement provided by Embodiment 1 of the present invention.

where 1—CMOS fixing device; 2—Stokes polarized CMOS sensor; 201—CMOS sensor; 202—Stokes analyzer; 3—optical lens sleeve; 4—optical magnifying glass; 5—aluminum alloy housing; 6—white diffused reflection coating; 7—lubricating oil flow channel; 8—optical glass; 9—circular polarized light source; 901—LED circuit board; 902—LED circular white light source; 903—linear polarizer; 10—lubricating oil branch; 11—equipment lubricating pipeline; 12—oil pump; 13—control terminal; 14—upper computer.

DETAILED DESCRIPTION OF THE EMBODIMENTS

The present invention is described in more detail with reference to the accompanying drawings and embodiments.

It should be noted that the following detailed description is exemplary and aims to further describe the present invention. Unless otherwise specified, all technical and scientific terms used herein have the same meanings as those generally understood by a person of ordinary skill in the art to which the present invention belongs.

The embodiments of the present invention and the features in the embodiments can be combined with each other in case of no conflict.

Embodiment 1

In this implementation, an imaging device for turbid oil abrasive particles based on polarized image enhancement is proposed. The following is a brief introduction to technical terms and related concepts involved in this processing scheme, where a CMOS sensor is a typical solid-state imaging sensor, which usually consists of several parts such as a pixel sensitive unit array, a row driver, a column driver, a timing control logic, an AD converter, a data bus output interface, and a control interface. These parts are usually integrated on the same silicon wafer, and a working process of the silicon wafer can generally be divided into resetting, photoelectric conversion, integration, and readout.

A specific working principle of the CMOS sensors is: external light illuminates a pixel array, causing a photoelectric effect and generating corresponding charges in pixel units. A row selection logic unit selects corresponding row pixel units as needed, and image signals in the row pixel units are transmitted to corresponding analog signal processing units and the A/D converter by means of signal buses of respective columns, and converted into digital image signals to be outputted, where the row selection logic unit can scan the pixel array line by line or perform interlaced scanning, and combined use of the row selection logic unit and a column selection logic unit can achieve a window extraction function of the images. Main functions of the analog signal processing units are to amplify the signals and increase a signal-to-noise ratio. In addition, in order to obtain practical cameras with qualified quality, a chip must contain various control circuits, such as exposure time control, and automatic gain control. In order to make each part of the circuits in the chip operate according to a prescribed pace, multiple timing control signals must be used. In order to facilitate the application of the cameras, it is also required that the chip can output some timing signals, such as synchronization signals, row start signals, and field start signals.

Raspberry Pi is a miniature single board computer known for its credit card-sized size and low-cost high-performance ARM processors. The Raspberry Pi can run multiple operating systems, such as Raspberry Pi OS (official), Ubuntu and Android, and has extensive scalability.

In addition, the Raspberry Pi has general purpose input/output (GPIO) pins that can be connected to various sensors, controllers, modules, etc., enabling programming control of hardware.

As described in the background art, abrasive particles contained in lubricating oil of rotating machinery equipment contain a large amount of equipment friction and abrasion information, reflecting the current abrasion status and health trend of the equipment. Capturing appearance characteristics of the abrasive particles in lubrication lines of equipment by an optical imaging method is a mainstream method for on-line abrasive particle monitoring. However, the lubricating oil will gradually become turbid and black due to oxidation and impurities over time, which poses difficulties for imaging and subsequent image processing of abrasive particles, seriously affecting accurate identification of the abrasion status of the equipment, reducing effective coverage duration of abrasive particle monitoring, and bringing bottlenecks for judging the development stage of abrasion of the equipment. In view of this, an anti-interference scattering-removal imaging device for abrasive particles described in the present invention, as shown in FIG. 1, specifically includes a CMOS fixing device 1, a Stokes polarized CMOS sensor 2, an optical lens sleeve 3, an optical magnifying glass 4, and an aluminum alloy housing 5.

Figure 2:
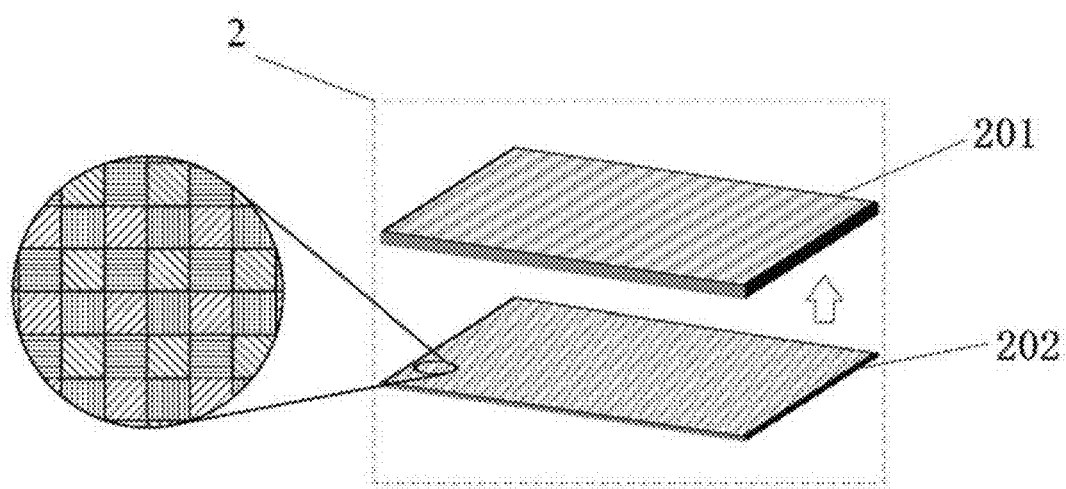
FIG. 2 is a schematic structural diagram of a Stokes polarized CMOS sensor provided by Embodiment 1 of the present invention.

As shown in FIG. 2, the Stokes polarized CMOS sensor 2 includes a CMOS sensor 201 and a Stokes analyzer 202, where the Stokes analyzer 202 contains multiple sets of linear polarization units in four polarization directions: 0°, 45°, 90°, and 135°. The Stokes analyzer 202 is used in combination with the CMOS sensor 201, and a single linear polarization unit corresponds to a single pixel of the CMOS sensor 201. That is, the entire CMOS can simultaneously obtain light information in four polarization directions. The optical lens sleeve 3 is combined with the CMOS fixing device 1 in a threaded manner, and the optical magnifying glass 4 is driven by rotating the optical lens sleeve 3 to adjust a focal length of the imaging system, achieving image plane focus of the Stokes polarized CMOS sensor 2. The resolution of the CMOS sensor 201 is 2592×1944 pixels, with a pixel element size of 1.4 microns. The optical magnification of the entire optical system is about 3.6. The CMOS fixing device 1 is fixed to the aluminum alloy housing 5 with a sealant.

Figure 3:
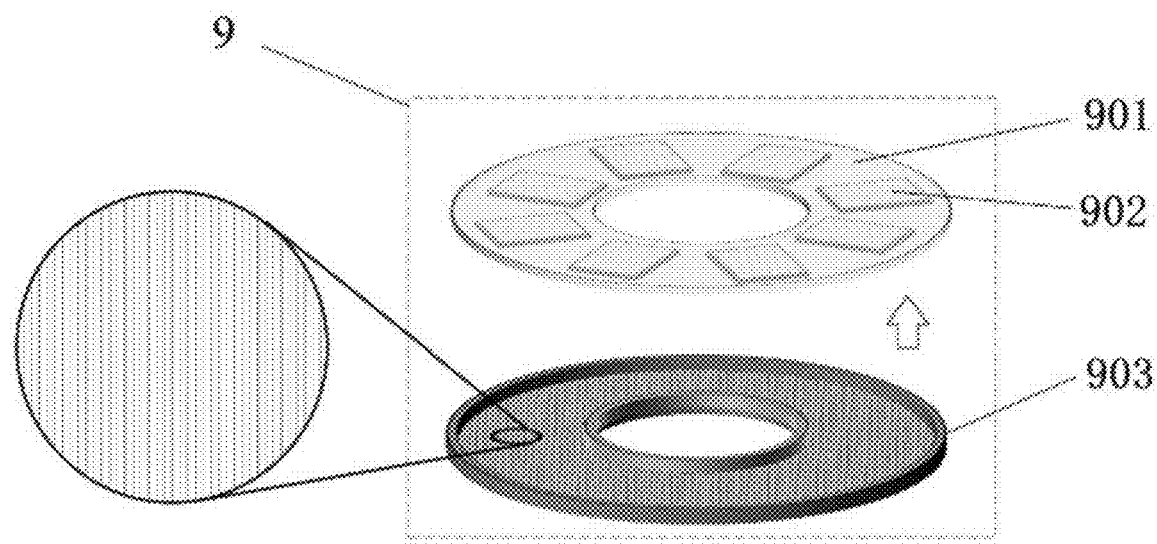
FIG. 3 is a schematic structural diagram of a circular polarized light source provided by Embodiment 1 of the present invention.

The circular polarized light source 9 is fixed inside the aluminum alloy housing 5, which includes an LED circuit board 901, eight sets of LED circular white light sources 902, and a linear polarizer 903 from top to bottom. As shown in FIG. 3, the LED circular white light sources 902 produce white light with color temperature of 6500K, and the intensity of light can be adjusted by voltage. The eight sets of LED circular white light sources 902 can ensure illumination uniformity of the light source. The light passes through the linear polarizer 903 and then changes from unpolarized natural white light to linearly polarized light with a specific polarization direction.

It can be understood that the aluminum alloy housing 5 in this implementation can also be replaced with hard housings made of other materials, such as a housing made of stainless steel or a housing made of hard plastic, which will not be described in detail here.

In this implementation, optical glass 8 having a 2 mm thickness is provided below the circular polarized light source 9, and is connected to the aluminum alloy housing 5 to form a gap having a 4 mm height as a lubricating oil flow channel 7. The lubricating oil carrying the abrasive particles flows in from an inlet of a left lubricating oil flow channel, passes through an imaging part and the lower part of a light source part area, and flows out from an outlet of a right lubricating oil flow channel. A white diffused reflection coating 6 is sprayed onto the bottom of the lubricating oil flow channel 7 to further ensure the uniformity of imaging illumination.

Embodiment 2

Figure 4:
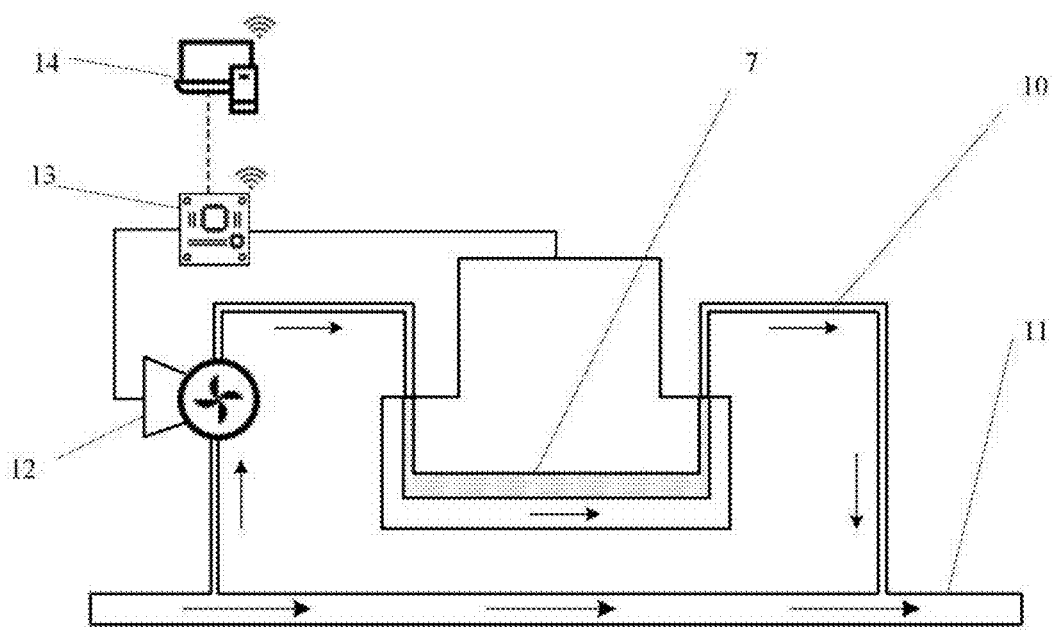
FIG. 4 shows a schematic diagram of an imaging system for turbid oil abrasive particles based on polarized image enhancement provided by Embodiment 2 of the present invention.

This implementation provides an imaging system for turbid oil abrasive particles based on polarized image enhancement, as shown in FIG. 4, an oil passage includes a monitored equipment lubricating pipeline 11, a lubricating oil branch 10, an oil pump 12, and a lubricating oil flow channel 7. To ensure that the imaging device in Embodiment 1 does not affect the normal operation of the monitored equipment lubricating system during monitoring of the lubricating oil of oil, in the present invention, the lubricating oil branch 10 is provided to be connected to the equipment lubricating pipeline 11, power is provided for the lubricating oil in the lubricating oil branch 10 through the oil pump 12, the normal uniform flow of the lubricating oil in the lubricating oil flow channel 7 is ensured, the maximum flow rate of the oil pump 12 is 200 ml/min, and the lubricating oil branch 10 is in sealed connection to the lubricating oil flow channel 7 through pipe threads. The control system includes a control terminal 13 (preferably using the Raspberry Pi) and an upper computer 14, where a monitoring program is stored in the Raspberry Pi, the Raspberry Pi is connected to the imaging device and the oil pump 12 through a GPIO interface to control start and stop of the above components and data transmission, and a remote connection module built in the Raspberry Pi can be connected to the upper computer 14 for data transmission or remote control.

Embodiment 3

This implementation provides an imaging method for turbid oil abrasive particles based on polarized image enhancement, using the imaging system for turbid oil abrasive particles based on polarized image enhancement according to Embodiment 2. An imaging principle is as follows:

in the imaging process of the abrasive particles, a part of light received by the Stokes polarized CMOS sensor 2 comes from background scattered light of oil scattering media, and another part of light comes from target signal light reflected by objects, i.e. I=B+T (1);
where I is the total light intensity entering the Stokes polarized CMOS sensor 2, T is the light intensity of target abrasive particles, and B is the background scattered light.

Any light has polarization characteristics, and light in any polarization status can be decomposed into two mutually orthogonal directions. Therefore, the above light can be respectively:

$$I = I_{//} + I_{\perp} \quad (2)$$
$$B = B_{//} + B_{\perp}$$
$$T = T_{//} + T_{\perp}$$

where $I_{//}$, $B_{//}$ and $T_{//}$ are components of the total light intensity, the background scattered light and the target signal light that are in the same vibration direction as incident light, $I_{\perp}$, $B_{\perp}$ and $T_{\perp}$ are components of the total light intensity, the background scattered light and the target signal light that are orthogonal to the vibration direction of the incident light.

Light intensities of all the light intensities entering the Stokes polarized CMOS sensor 2, that are in the same vibration direction or orthogonal to the vibration direction as the incident light are:

$$I_{//} = B_{//} + T_{//} \quad (3)$$
$$I_{\perp} = B_{\perp} + T_{\perp}$$

Polarization difference imaging utilizes an image difference between two mutually orthogonal polarization directions to eliminate the background scattered light. The differentiated light intensity is:

$$I_{PD} = I_{//} - I_{\perp} \quad (4)$$
$$= (B_{//} + T_{//}) - (B_{\perp} + T_{\perp});$$
$$= T_{//} - T_{\perp} + B_{//} - B_{\perp}$$

as long as formula (4) satisfies that $B_{//}$ and $B_{\perp}$ components are equal, that is, when included angles between the two orthogonal polarization directions and the direction of the background scattered light are 45° respectively, difference filtering out of the background scattered light can be achieved (due to material differences, the polarization directions of the target abrasive particle light T and the background scattered light B are different). Only the information of the target abrasive particle light T is retained in $I_{PD}$. However, by the above polarization difference imaging method, the analyzer needs to be rotated by 90° to shoot two images in a horizontal direction and in a vertical direction for calculation, which is low in efficiency and large in difficulty. Therefore, the present invention introduces a real-time polarization difference imaging principle on the basis of Stokes vectors for design on this basis.

The Stokes vectors are a mainstream method for characterizing polarized light. The Stokes vectors of a beam can be calculated from the polarized images in four polarization directions: 0°, 45°, 90°, and 135°. The intensities of these four images can be represented as I (0), I (45), I (90), and I (135), respectively. The Stokes vectors can be represented as:

$$S = \begin{bmatrix} S_0 \\ S_1 \\ S_2 \end{bmatrix} = \begin{bmatrix} I(0) + I(90) \\ I(0) - I(90) \\ I(45) - I(135) \end{bmatrix}; \quad (5)$$

where $S_0$ represents the total light intensities of a horizontal linear polarization component (i.e. A 0° linear polarization component) and a vertical linear polarization component (i.e. A 90° linear polarization component), $S_1$ represents a light intensity difference between the horizontal linear polarization component and the vertical linear polarization component, and $S_2$ represents a light intensity difference between the 45° linear polarization component and the 135° linear polarization component.

A Mueller matrix set corresponding to the analyzers whose polarization directions are respectively at 45° to the polarization direction $\theta_B$ of the background light and whose transmission directions are mutually orthogonal can be expressed as:

$$M_{//} = \begin{pmatrix} 1 & -\sin(2\theta_B) & \cos(2\theta_B) & 0 \\ -\sin(2\theta_B) & \sin^2(2\theta_B) & -\sin(2\theta_B)\cos(2\theta_B) & 0 \\ \cos(2\theta_B) & -\sin(2\theta_B)\cos(2\theta_B) & \cos^2(2\theta_B) & 0 \\ 0 & 0 & 0 & 0 \end{pmatrix} \quad (6)$$

$$M_{\perp} = \begin{pmatrix} 1 & \sin(2\theta_B) & -\cos(2\theta_B) & 0 \\ \sin(2\theta_B) & \sin^2(2\theta_B) & -\sin(2\theta_B)\cos(2\theta_B) & 0 \\ -\cos(2\theta_B) & -\sin(2\theta_B)\cos(2\theta_B) & \cos^2(2\theta_B) & 0 \\ 0 & 0 & 0 & 0 \end{pmatrix};$$

the relationship between the polarization status $S_{in}$ of the incident light and the polarization status $S_{out}$ of the light after action by the analyzers is $S_{out}=M \cdot S_{in}$ (7);

it can be known that the intensity of the background light and the intensity of the target signal light after action by the analyzers can be expressed as:

$$I_{//}(B) = [I(B) + S_1(B)\sin2\theta_B - S_2(B)\cos2\theta_B]/2 \quad (8)$$
$$I_{\perp}(B) = [I(B) - S_1(B)\sin2\theta_B + S_2(B)\cos2\theta_B]/2$$
$$I_{//}(B) = [I(T) + S_1(T)\sin2\theta_B - S_2(T)\cos2\theta_B]/2 ;$$
$$I_{\perp}(B) = [I(T) - S_1(T)\sin2\theta_B + S_2(T)\cos2\theta_B]/2$$

combining the relationship $$\theta_B = \frac{1}{2}\arctan\frac{S_1(B)}{S_2(B)} \quad (9)$$

(between the angle of a polarization direction and the Stokes vectors;

the intensity of the polarization difference image can be obtained as:

$$I_{PD} = I_{//} - I_{\perp} \quad (10)$$
$$= T_{//} - T_{\perp} + B_{//} - B_{\perp} ;$$
$$= S_1(T)\sin2\theta_B - S_2(T)\cos2\theta_B$$

it can be seen from formula (10) that a final polarization difference image only contains Stokes vectors related to the intensity of the target signal light; and to filter out the background scattered light, the entire process requires obtaining the Stokes vectors of the light and the angle of polarization of the background scattered light.

In the present invention, a Stokes polarized camera is used for acquiring the Stokes vectors. The main difference between the polarized camera and a conventional camera is that a micro analyzer is mounted on an outer layer of the CMOS, as shown in FIG. 2, the structure can ensure that each pixel can only receive one of the four polarization directions of 0°, 45°, 90°, and 135°. Each image can be decomposed into four linear polarization intensity images I (0), I (45), I (90), and I (135) through a pixel segmentation algorithm, and videos can be shot, greatly improving the efficiency of polarization difference imaging. The angle of polarization of the background scattered light is calculated by calculating the angle of a polarization direction of each pixel, and the angle of a polarization direction with the highest occurrence probability is approximated as the angle of polarization of the background scattered light.

Figure 5:
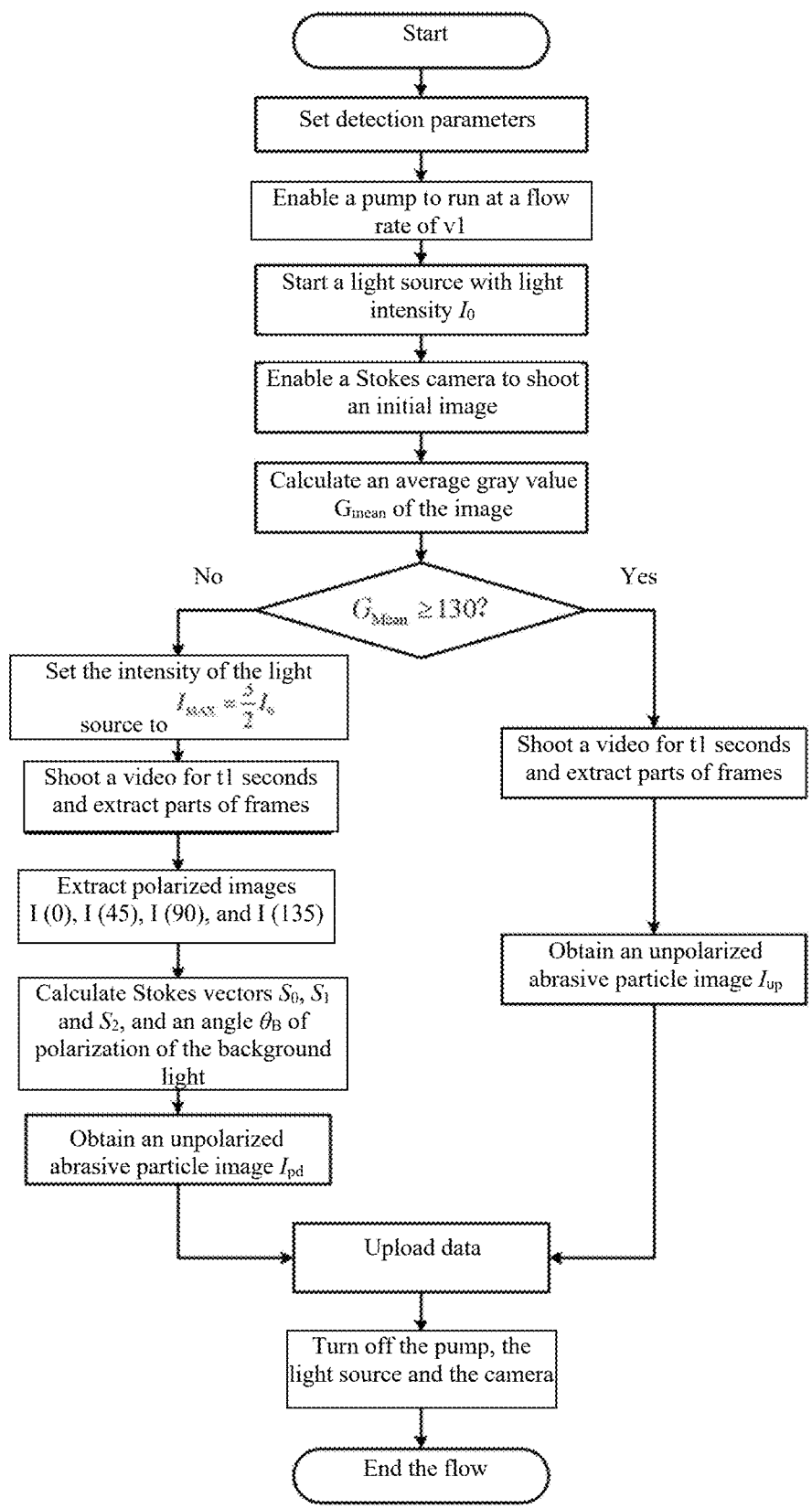
FIG. 5 shows a schematic diagram of a flowchart of an imaging method for turbid oil abrasive particles based on polarized image enhancement provided by Embodiment 3 of the present invention.

FIG. 5 shows a method flow of polarized imaging of oil abrasive particles. Firstly, monitoring parameters are set through the upper computer 14, including the flow rate $v_1$ of the oil pump 12, the initial light intensity $I_0$ of the circular polarized light source 9, a video shooting duration $t_1$, etc. The optical lens sleeve 3 is manually adjusted for focusing. As an abrasive particle size range for monitored oil abrasive particles is usually between 10-200 microns, the abrasive particles will stick to the bottom of the lubricating oil flow channel 7 and the upper part of the white diffused reflection coating 6 at slower oil flow rates. Therefore, during focusing, a focal plane needs to be set in this area to ensure clarity of the majority of the abrasive particles; then, the Raspberry Pi controls the oil pump 12, the Stokes polarized CMOS sensor 2 and the circular polarized light source 9 to start, then, the Stokes polarized CMOS sensor 2 shoots the initial image, and the Raspberry Pi reads the images and performs graying according to the formula:

$$G_{Mean} = \frac{1}{MN}\sum_{i=0}^{M-1}\sum_{j=0}^{N-1}I(i,j); \quad (11)$$

an average gray value of the initial image is calculated, in the formula, M is a height of the image, N is a width of the image, and I (i, j) represents the gray value of a pixel with coordinates (i, j) in the image; then the average gray value $G_{Mean}$ is judged:

if $G_{Mean} \geq 130$, it indicates that the overall brightness of the oil abrasive particle image is relatively high, reflected light generated by the white diffused reflection coating 6 contributes major light intensity, indicating that oil is relatively clear, and a light scattering effect is disregarded; at this time, an imaging flow of normal oil abrasive particles is initiated: the Stokes polarized CMOS sensor 2 records a video for a duration of t1 and saves the video in the Raspberry Pi, and parts of frames are extracted from the video to obtain an unpolarized abrasive particle image $I_{up}$;

if $G_{Mean} < 130$, it indicates that the overall brightness of the image is dark, the oil is dark in color and high in turbidity, light generated by a light source is scattered by the turbid oil, and the intensity of the returned light is greatly reduced; at this time, an imaging flow of the turbid oil abrasive particles is initiated: firstly, the light intensity of the circular polarized light source 9 is increased to $$I_{MAX} = \frac{3}{2}I_0$$

so as to compensate for scattering loss of light and improve the brightness of the image; the Stokes polarized CMOS sensor 2 records a video for a duration of t1 and saves the video in the Raspberry Pi, parts of frames are extracted from the video, and a single-frame image is decomposed into four images: I (0), I (45), I (90), and I (135) according to a pixel arrangement order; stokes vectors $S_0$, $S_1$ and $S_2$ are calculated, and distribution probability of angle of polarizations θ of each pixel is calculated; the angle of polarization with the highest occurrence probability is selected as an angle of polarization $\theta_B$ of the background light; and finally, a polarization difference image $I_{PD}$ corresponding to each video frame is obtained, after the imaging flow is completed, image data is uploaded to an upper computer 14, the Raspberry Pi turns off the oil pump 12, the Stokes polarized CMOS sensor 2, and the circular polarized light source 9, and a working flow is completed.

Figure 6:
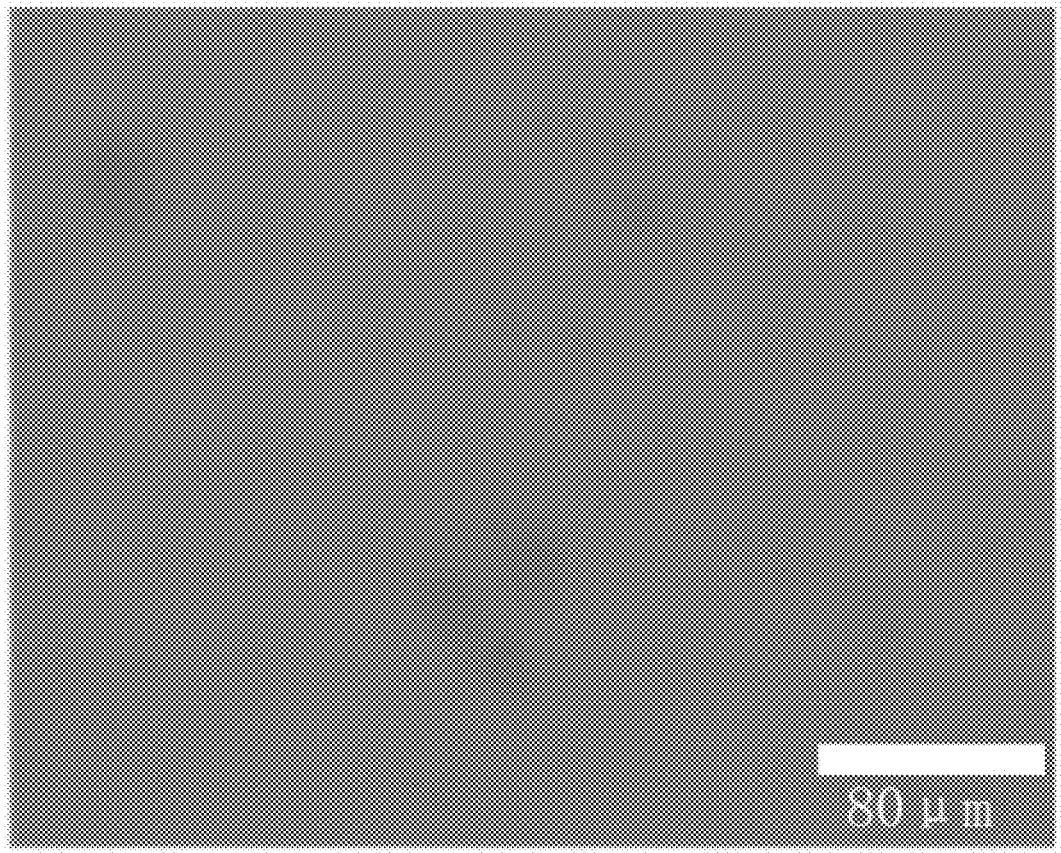
FIG. 6 shows a schematic diagram of imaging quality of abrasive particles in turbid oil monitored by the current on-line abrasive particle sensor provided by Embodiment 3 of the present invention.
Figure 7:
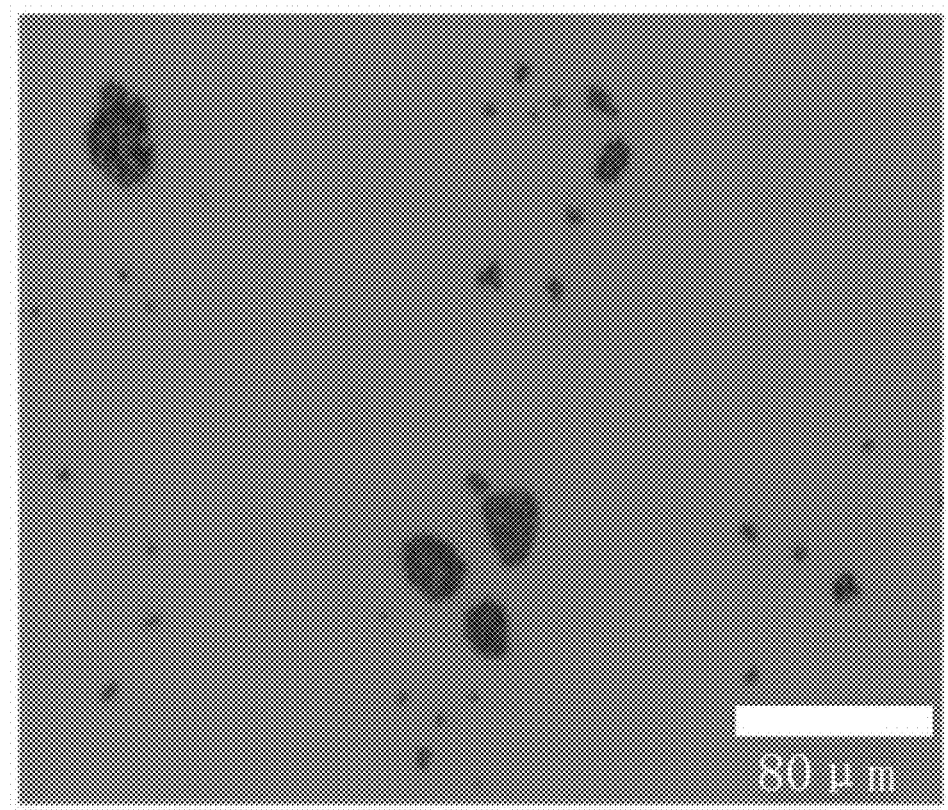
FIG. 7 is a schematic diagram of polarization difference imaging quality of abrasive particles in the same scene provided by Embodiment 3 of the present invention.
Figure 8:
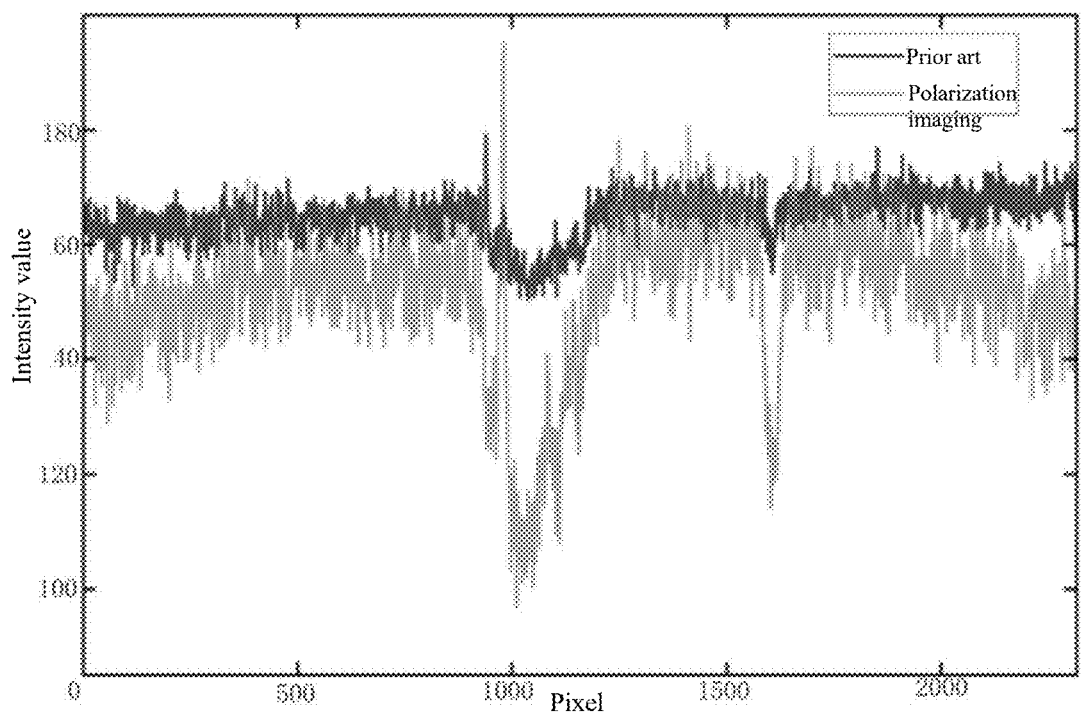
FIG. 8 shows a schematic diagram comparing imaging quality of turbid oil between the prior art and the present invention provided by Embodiment 3 of the present invention.

FIG. 6 shows the imaging quality of the abrasive particles in turbid oil monitored by the current on-line abrasive particle sensor. Due to the mixing and overlaying interference of scattered light from the oil background and target reflected light from the abrasive particles, the edges of the abrasive particles having a larger size are blurred, the texture information of the abrasive particles cannot be captured, and the abrasive particles having a smaller size are almost invisible, which will affect subsequent analysis and processing of the abrasive particle images and judgment of the abrasion status of the equipment; FIG. 7 shows polarization difference imaging quality of the abrasive particles in the same scene, edges and textures of the abrasive particles are clear, and the abrasive particles being small in size can be distinguished, which can meet the needs of subsequent abrasive particle recognition and information extraction steps; and FIG. 8 shows results of analyzing pixel intensity of a certain horizontal section on the images by the two methods mentioned above. An intensity curve of imaging in the prior art has a small fluctuation amplitude, indicating that image contrast between areas where the abrasive particles exist having low intensity values and background areas is low, and the abrasive particles are not prominent in targets. On the contrary, an intensity curve of the images acquired by a polarization imaging technology has a large drop in abrasive particle target areas, the image contrast between the areas where the abrasive particles exist and the background areas is high, and the abrasive particles are prominent in targets.

The foregoing is merely illustrative of the preferred embodiments of the present invention and is not intended to limit the present invention, and various changes and modifications may be made by those skilled in the art. Any modifications, equivalent replacements, improvements, etc. made within the spirit and principle of the present invention shall fall within the protection scope of the present invention.

What is claimed is:

1. An imaging system for turbid oil abrasive particles based on polarized image enhancement, comprising
an equipment lubricating pipeline, a lubricating oil branch, an oil pump, a control terminal, and an imaging device for turbid oil abrasive particles based on polarized image enhancement, wherein
the equipment lubricating pipeline is in communication with the lubricating oil branch, the oil pump is connected to the lubricating oil branch, and the lubricating oil branch is in communication with an inlet and an outlet of a lubricating oil flow channel, and then is in communication with the equipment lubricating pipeline;
the control terminal is connected to a Stokes polarized CMOS sensor and the oil pump, respectively;
the imaging device for turbid oil abrasive particles based on polarized image enhancement comprises a CMOS fixing device, the Stokes polarized CMOS sensor, an optical lens sleeve and an optical magnifying glass, wherein the Stokes polarized CMOS sensor comprises a CMOS sensor and a Stokes analyzer;
the Stokes analyzer comprises a plurality of linear polarization units in different polarization directions, and all the linear polarization units are in one-to-one correspondence in pixels with the CMOS sensor;
the optical lens sleeve is connected to the CMOS fixing device, the optical magnifying glass is provided at a tail end of the optical lens sleeve, and the CMOS fixing device is fixedly connected to a housing;
a circular polarized light source is fixed inside the housing, optical glass connected to the inner wall of the housing is provided below the circular polarized light source, a gap between the bottom of the optical glass and the inner wall of the housing serves as the lubricating oil flow channel, and the inlet and the outlet of the lubricating oil flow channel are both formed in the housing;
a white diffused reflection coating is sprayed onto the flow channel bottom of the lubricating oil flow channel, the circular polarized light source comprises a circuit board, a circular white light source and a linear polarizer from top to bottom, the circuit board is connected to the circular white light source, and light from the circular white light source passes through the linear polarizer and changes from unpolarized natural white light to linearly polarized light with a specific polarization direction;
the intensity of background light and the intensity of target signal light after action by the analyzer can be expressed as:

$$I_{//}(B) = [I(B) + S_1(B)\sin 2\theta_B - S_2(B)\cos 2\theta_B]/2$$
$$I_\perp(B) = [I(B) - S_1(B)\sin 2\theta_B + S_2(B)\cos 2\theta_B]/2$$
$$I_{//}(T) = [I(T) + S_1(T)\sin 2\theta_B - S_2(T)\cos 2\theta_B]/2$$
$$I_\perp(T) = [I(T) - S_1(T)\sin 2\theta_B + S_2(T)\cos 2\theta_B]/2$$

a relationship between a polarization direction $\theta_B$ of background light and Stokes vectors is:

$$\theta_B = \frac{1}{2}\arctan\frac{S_1(B)}{S_2(B)},$$

wherein $S_1$ (B) is a light intensity difference between a 0° polarization component and a 90° polarization component of background scattered light, and $S_2$ (B) is a light intensity difference between a 45° polarization component and a 135° polarization component of the background scattered light;
an image IPD of polarized abrasive particles is: IPD=S1 (T) sin 2 $\theta_B$–S2 (T) cos 2 $\theta_B$, wherein S1 (T) is a light intensity difference between a 0° polarization component and a 90° polarization component of the target signal light, S2 (T) is a light intensity difference between a 45° polarization component and a 135° polarization component of the target signal light, and $\theta_B$ is a polarization direction of the background light;

a final polarization difference image only contains Stokes vectors related to the intensity of the target signal light; to filter out the background scattered light, the entire process requires obtaining the Stokes vectors of the light and the angle of polarization of the background scattered light;

the oil pump operates at a set speed and starts the circular polarized light source with first set light intensity, the Stokes polarized CMOS sensor acquires an initial image and calculates an average gray value $$G_{Mean} = \frac{1}{MN} \sum_{i=0}^{M-1} \sum_{j=0}^{N-1} I(i,j)$$

of the initial image, in the formula, M is a height of the image, N is a width of the image, and I (i, j) represents the gray value of a pixel with coordinates (i, j) in the image; then the average gray value $G_{Mean}$ is judged:

if $G_{Mean} \geq 130$, it indicates that the overall brightness of the oil abrasive particle image is relatively high, reflected light generated by the white diffused reflection coating contributes major light intensity, indicating that oil is relatively clear, and a light scattering effect is disregarded; at this time, an imaging flow of normal oil abrasive particles is initiated: the Stokes polarized CMOS sensor records a video for a duration of t1 and saves the video in the Raspberry Pi, and parts of frames are extracted from the video to obtain an unpolarized abrasive particle image $I_{up}$;

if $G_{Mean} < 130$, it indicates that the overall brightness of the image is dark, the oil is dark in color and high in turbidity, light generated by a light source is scattered by the turbid oil, and the intensity of the returned light is greatly reduced; at this time, an imaging flow of the turbid oil abrasive particles is initiated: firstly, the light intensity of the circular polarized light source is increased to $I_{MAX}=3/2I_0$ so as to compensate for scattering loss of the light and improve the brightness of the image; the Stokes polarized CMOS sensor records a video for a duration of t1 and saves the video in the Raspberry Pi, parts of frames are extracted from the video, and a single-frame image is decomposed into four images: I (0), I (45), I (90), and I (135) according to a pixel arrangement order; stokes vectors S0, S1 and S2 are calculated, and distribution probability of angle of polarizations of each pixel is calculated; the angle of polarization with the highest occurrence probability is selected as an angle of polarization of the background light; and finally, a polarization difference image corresponding to each video frame is obtained, after the imaging flow is completed, image data is uploaded to an upper computer, the Raspberry Pi turns off the oil pump, the Stokes polarized CMOS sensor, and the circular polarized light source, and a working flow is completed.

2. The imaging system for turbid oil abrasive particles based on polarized image enhancement according to claim 1, wherein different polarization directions are the 0° polarization direction, the 45° polarization direction, the 90° polarization direction, and the 135° polarization direction.

3. The imaging system for turbid oil abrasive particles based on polarized image enhancement according to claim 1, wherein the housing is an aluminum alloy housing.

4. The imaging system for turbid oil abrasive particles based on polarized image enhancement according to claim 1, wherein the control terminal is in wired communication connection or wireless communication connection with the upper computer.

5. An imaging method for turbid oil abrasive particles based on polarized image enhancement, using the imaging system for turbid oil abrasive particles based on polarized image enhancement according to claim 1, comprising the following process:

the oil pump operates at a set speed and starts the circular polarized light source with first set light intensity, and the Stokes polarized CMOS sensor acquires an initial image and calculates an average gray value of the initial image:

if the average gray value is less than a set threshold, the light intensity of the circular polarized light source is adjusted to second set light intensity, after set time of shooting, image frames are extracted, polarized images are extracted according to the image frames, the Stokes vectors and the angle of polarization of the background light are calculated, and the polarized abrasive particle image is obtained according to the Stokes vectors and the angle of polarization of the background light; and if the average gray value is greater than or equal to the set threshold, after set time of shooting, the image frames are extracted, and the unpolarized abrasive particle image is obtained according to the image frames.

6. The imaging method for turbid oil abrasive particles based on polarized image enhancement according to claim 5, wherein the polarized images are images in the 0° polarization direction, images in the 45° polarization direction, images in the 90° polarization direction, and images in the 135° polarization direction, the first set light intensity is $I_0$, and the second set light intensity is $$\frac{3}{2}I_0.$$

* * * * *